United States Patent
Upmeier et al.

(10) Patent No.: US 7,351,799 B2
(45) Date of Patent: Apr. 1, 2008

(54) USE OF INTRAMOLECULARLY, COVALENTLY CROSS-LINKED PROTEINS AS BINDING PARTNERS IN IMMUNOASSAYS

(75) Inventors: Barbara Upmeier, Iffeldorf (DE); Dittmar Schlieper, Iffeldorf (DE); Frederic Donie, Penzberg (DE)

(73) Assignee: Roche Diagnostic Operations, Inc., Indianapolis, IN (US)

( * ) Notice: Subject to any disclaimer, the term of this patent is extended or adjusted under 35 U.S.C. 154(b) by 117 days.

(21) Appl. No.: 10/447,129

(22) Filed: May 28, 2003

(65) Prior Publication Data

US 2004/0137425 A1 Jul. 15, 2004
US 2007/0281293 A9 Dec. 6, 2007

Related U.S. Application Data

(63) Continuation of application No. PCT/EP01/13780, filed on Nov. 27, 2001.

(30) Foreign Application Priority Data

Nov. 30, 2000 (DE) .................. 100 59 720

(51) Int. Cl.
*C07K 14/00* (2006.01)
(52) U.S. Cl. ..................... 530/350; 530/402
(58) Field of Classification Search ............. 435/5, 435/7.1, 7.92
See application file for complete search history.

(56) References Cited

U.S. PATENT DOCUMENTS 5,258,501 A * 11/1993 Barbaric et al. ............ 530/395
7,037,894 B2 5/2006 Marshall et al.

FOREIGN PATENT DOCUMENTS

| DE | 2615349 A | 10/1976 |
|---|---|---|
| EP | 0331068 B1 | 9/1989 |
| WO | WO 98/40744 | 9/1998 |

OTHER PUBLICATIONS

Hornbeck, P., "Assays for Antibody Production: Enzyme-Linked Immunosorbent Assays"In: Current Protocols in Immunology (1991) 2.1.1-2.1.22.*

"Antibody Structure" downloaded from http://webarchive.org/web/20000929210635/http://ntri.tamuk.edu/immunology/ab-structure.html on Tuesday, Dec. 7, 2004.*

Debyser, Zeger et al., "Chemical crosslinking of the subunits of HIV-1 reverse transcriptase," Protein Science (1996), 5:278-286.*

Ishikawa et al., "Whole Saliva Dried on Filter Paper for Diagnosis of HIV-1 Infection by Detection of Antibody IgG to HIV-1 With Ultrasensitive Enzyme Immunoassay Using Recombinant Reverse Transcriptase . . . ," Jrnl of Clinical Lab Analysis 10:35-41 (1996).*

Ishikawa, Setsuko et al., "Whole Saliva Dried on Filter Paper for Diagnosis of HIV-1 Infection by Detection of Antibody IgG to HIV-1 With Ultrasensitive Enzyme Immunoassay Using Recombinant Reverse Transcriptase as Antigen," Journal of Clinical Laboratory Analysis 10:35-41 (1996).

"Immunology", Janis Kuby, 1994, W.H. Freeman & Company, New York. (S. 113, Fig. 5-4)

"Crosslinks Between Intramolecular Pairs of Ferritin Subunits: Effects on Both H and L Subunits and on Immunoreactivity of Sheep Spleen Ferritin," Arch Biochem Biophys. Jul. 1989, 272(1):88-96.

"Detection of Anti-Human Immunodeficiency Virus Type 1 (HIV-1) Immunoglobulin G in Urine by an Ultrasensitive Enzyme Immunoassay (Immune Complex Transfer Enzyme Immunoassay) with Recombinant Reverse Transcriptase as an Antigen," Hashinaka et al., J. Clin. Microbio., 32, 819-822 (1994).

Kuo, Kou-Wha et al., "Immunochemical Characterization of αBungarotoxin Detoxified with Glutaraldehyde," J. Medical Science 6:408-417, 1990.

Muller, Barbara et al., "Co-expression of the Subunits of the Heterodimer of HIV-1 Reverse Transcriptase in *Escherichia coli*," The Journal of Biological Chemistry, vol. 26, No. 24, Aug. 25, 1989, 13975-13978.

"Immunoglubin Fine Structure," p. 113 (1997).

* cited by examiner

*Primary Examiner*—Bruce R. Campell
*Assistant Examiner*—Nico Kinsey White
(74) *Attorney, Agent, or Firm*—Barnes & Thornburg LLP

(57) ABSTRACT

The invention concerns the use of intramolecularly, covalently cross-linked proteins and covalently cross-linked reverse transcriptase from HIV as immunological binding partners in immunoassays. It also concerns immunological test procedures for detecting an analyte in a sample in which intramolecularly, covalently cross-linked proteins are used as binding partners, and it further concerns intramolecularly, covalently cross-linked reverse transcriptase from HIV and a method for producing this reverse transcriptase.

12 Claims, 1 Drawing Sheet

USE OF INTRAMOLECULARLY, COVALENTLY CROSS-LINKED PROTEINS AS BINDING PARTNERS IN IMMUNOASSAYS

RELATED APPLICATIONS

This application is a continuation of international application PCT/EP01/13780, filed Nov. 27, 2001 which claims priority to German application DE 10059720.3, filed Nov. 30, 2000.

FIELD OF THE INVENTION

The present invention concerns the use of intramolecularly, covalently cross-linked proteins, and in particular, the use of covalently cross-linked reverse transcriptase (RT) from HIV as immunological binding partners in immunoassays, and to immunological test procedures for detecting an analyte in a sample in which intramolecularly, covalently cross-linked proteins are used as binding partners. It also concerns intramolecularly, covalently cross-linked reverse transcriptase from HIV and a method for producing this reverse transcriptase.

BACKGROUND OF THE INVENTION

The use of proteins as binding partners for the detection of analytes in immuno-diagnostic test procedures has been known for a long time. In all conventional immunoassays, the sample is incubated with one or more binding partners that are specific for the analyte. The binding partner or binding partners bind(s) specifically to the analyte to be detected. In the case of an antibody test, for example, in the case of an HCV infection, the sample to be examined is, for example, contacted with an HCV antigen which specifically binds the anti-HCV antibody to be detected. In an antigen test, for example, for detecting the tumour marker prostate-specific antigen (PSA), the sample is contacted with antibodies which specifically bind the PSA in the sample.

Subsequently the analyte is detected in all immunoassays. This can, for example, be carried out by binding and subsequently detecting another binding partner provided with a detectable label which binds to the complex consisting of analyte and immunological binding partner.

In general the immunoassays are carried out in a heterogeneous or homogeneous test format. The heterogeneous test formats are frequently carried out as sandwich or bridge tests. Competitive methods are also well known in which either the analyte or the specific binding partner is displaced from the complex of analyte and specific binding partner by, for example, adding a labelled analyte analogue.

In all immunological test methods, it is important that the reactants used as the specific immunological binding partners are present in a stable form and that they are not destroyed, for example, by unfavourable storage conditions. This risk can occur in particular when the proteins used as specific binding partners are composed of several subunits. The subunits can be held together covalently, for example, by means of disulfide bridges, or non-covalently, for example, by means of hydrogen bridges, opposite charges, and/or hydrophobic interactions.

In some cases, the materials required for the immunological test may become unstable and denature under the storage conditions (for example, as a liquid reagent) in the working solutions prepared for the test or during the immunological reaction itself. As a result, the tertiary and the quaternary structure of the protein may be changed in such a manner that the substance can no longer be used in the immunoassay.

The subunit components of the proteins used as a specific binding pair may separate under unfavourable conditions. This dissociation of subunits may, for example, be caused by the reduction of disulfide bridges by common buffer additives such as DTT in the case of natural covalent bridges.

However, the risk of dissociation is even higher in the case of non-covalently linked subunits of a protein which are held together by charges or hydrophobic interactions. The subunits of such proteins can be very easily dissociated even by common buffer additives such as salts, detergents, or unfavourable variations in pH and temperature. An individual and hence unprotected subunit is thus also susceptible to denaturation. This may lead to major changes in the tertiary structure of the protein or of the individual subunit. This also means that the immunological properties such as the accessibility of important epitopes is changed to such an extent that the protein used as a binding partner in the immunoassay is no longer recognized immunologically and is hence no longer specifically bound.

Another risk of subunit dissociation is that subunits provided with different labelling groups may re-associate due to the adjustment of the chemical equilibrium. If in a specific case, a protein composed of two subunits for use in an antibody test in a bridge test format is derivatized in order to be used as a universal solid phase and, on the other hand, the same protein is also used as a signal-generating component and for this purpose is coupled to a label (e.g., an enzyme, fluorescent label, or chemiluminescent label), the following may happen: a calibration curve which is initially generated with positive samples (samples which contain the analyte) becomes flatter as time progresses. The signals for negative samples (blank values) increase and increasingly approximate the values for the upper positive samples so that it is no longer possible to differentiate between analyte-free and analyte-containing samples.

A method for chemically modifying enzymes by reaction with quinones is described in German Patent Application DE 26 15 349. These modifications increase the stability which results in an improved enzyme activity. It is mentioned that the enzyme molecules can be cross-linked to one another, i.e., intermolecularly and also intramolecularly. In this case, the preservation of immunoreactive epitopes is irrelevant. The use of enzymes modified with quinones in immunodiagnostic methods is not described.

Debyser and De Clercq (Protein Science 5, p. 278-286, 1996) describe the cross-linking of the two subunits of HIV-1 reverse transcriptase by means of dimethyl suberimidate which cross-links lysine side chains. The purpose of the cross-linking is to examine the dimerization of the two RT subunits. Only the dimeric RT is enzymatically active. The two subunits are covalently cross-linked in the presence of various inhibitors. RT molecules and multimers that are more or less strong cross-linked depending on the effectiveness of the inhibitor are formed after the chemical cross-linking reaction. The effect of the cross-linking on immunologically relevant epitopes or the use of cross-linked molecules in immunoassays is unimportant.

The use of intermolecularly cross-linked immunoglobulins in immunoassays is disclosed in EP-A-0 331 068. This means that several immunoglobulin molecules or fragments thereof are covalently linked together. The multimers of antibodies and fragments thereof are used as an interference-reducing reagent. The cross-linked immunoglobulins and fragments thereof are intended to eliminate interfering factors of human serum that are directed towards immunoglobulins.

The cross-linked proteins described in the prior art, which are composed of several subunits under natural conditions, are unsuitable or of only limited suitability for use as antigens or immunological binding partners since, in general, intermolecular multimers consisting of several protein molecules are formed. These multimers are of only limited use for immunoassays since they usually do not have a defined size. Hence the multimers have a random distribution of sizes, i.e., mono-, di-, tri-, tetramers, etc. are present together in one mixture. The undefined cross-linking may mask the epitopes. Consequently a sample antibody to be detected may not be able to bind to the masked epitope of the antigen, and hence a false negative result is obtained.

Another problem with using multimers as immunological binding partners is the fact that there is an increased risk that interfering factors present in the sample may bind unspecifically to the multimeric proteins. Interfering factors such as rheumatoid factors often have several binding sites of low affinity. If multimeric proteins are then used as immunological binding partners, this may have the effect that especially the interfering factors find many targets, i.e., binding sites on the multimeric proteins. This may lead to false positive test results, and the overall specificity of the immunoassay is greatly reduced.

SUMMARY OF THE INVENTION

Hence the object was to provide proteins with an improved stability which can be used in immunoassays as binding partners. The proteins improved in this manner should have good epitope accessibility, and the specificity of the immunological test procedure in which the proteins are used should be maintained.

The object is achieved by the invention described in the independent claims. The dependent claims represent preferred embodiments.

It surprisingly turned out that proteins that are almost exclusively intramolecularly cross-linked can be produced without loss of their immunological properties, and these proteins can be used in an advantageous manner in immunological test procedures as immunological binding partners. The stability problems that occur when the proteins are not cross-linked are thus substantially avoided. Hence the invention concerns the use of intramolecularly, covalently cross-linked proteins as immunological binding partners in immunological test procedures.

DETAILED DESCRIPTION OF THE INVENTION

Figure 1:
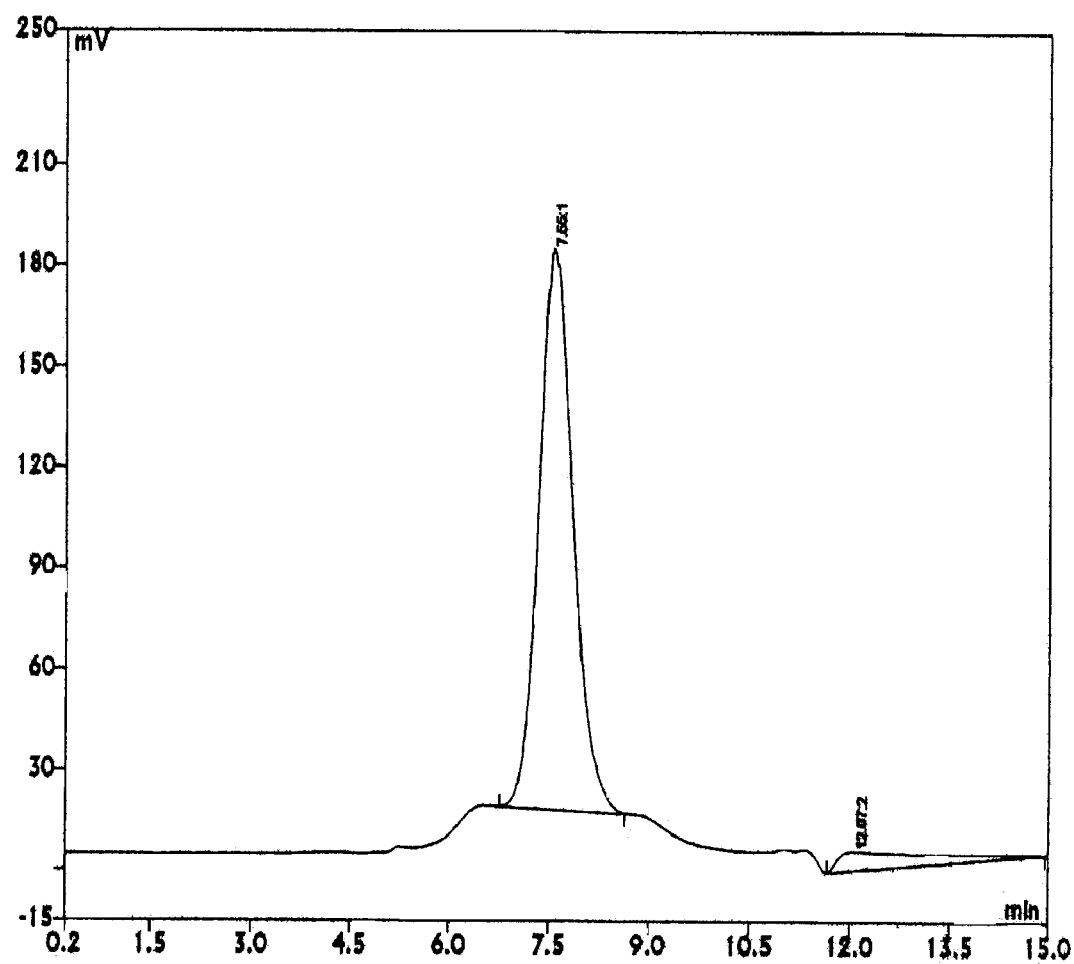
FIG. 1 shows the analysis by gel permeation chromatography of the molecular weights of RT obtained after cross-linking.

All proteins required for immunological test procedures that are familiar to a person skilled in the art can be used as the proteins. All polypeptides can be used which could, as a result of their folding, i.e., their tertiary or quaternary structure, have a tendency to unfold, to denature, or to dissociate into various subunits under the conditions of an immunoassay. When such a structural change occurs, there is a risk that immunologically important epitopes are changed in such a manner that, for example, they are no longer specifically bound by antibodies. In the worst case, this means that an immunological test result is negative, i.e., it does not indicate the presence of the antibody to be detected because the proteins used as binding partners are denatured. These disadvantages are substantially avoided by the use of intramolecularly, covalently cross-linked proteins according to the invention.

In particular, those intramolecularly, covalently cross-linked proteins are used which are naturally composed of several subunits. DNA or RNA polymerases, particularly the reverse transcriptase from HIV, and especially preferably the reverse transcriptase from HIV-1 are preferably used.

The proteins can be from any desired source. The proteins to be cross-linked can be isolated from their natural source such as an organism or virus. However, the use of recombinant proteins produced by genetic engineering is preferred. A recombinant purified RT is especially preferably used which is expressed by an expression clone as described, for example, in Müller et al., J. Biol. Chem. 264/24:13975-13978 (1989).

With the intramolecularly, covalently cross-linked proteins, it is important that the epitopes that are important for immunological recognition are not changed by the cross-linking or only so slightly that the other immunological binding partner in the test recognizes and specifically binds the cross-linked protein just as well as the uncrosslinked protein. Hence the cross-linking should not generate any immunologically relevant artefacts that could falsify the test result.

The "protein" refers to all polypeptides which are composed of at least about 50 amino acids, preferably of at least 100 amino acids. The term protein also includes modified proteins such as proteins that are linked with sugar residues, sialic acids, or lipid structures.

The term "intramolecularly, covalently cross-linked" refers to proteins whose polypeptide chain has been linked together by chemical modification in such a manner that it can no longer unfold, i.e., it can no longer lose its tertiary structure and thus the accessibility of important epitopes. In the case of a protein which is composed of several subunits, the intramolecular, covalent cross-linking maintains the tertiary as well as the quaternary structure. The modification prevents the various polypeptide chains from diffusing away from one another.

It is important that the covalent linkage only occurs within a protein molecule. In the case of proteins which are only composed of one polypeptide chain and thus of only one subunit under natural conditions, at least two sites within a polypeptide chain are linked. Hence no oligomers consisting of several proteins are formed by the intramolecular, covalent cross-linking. Such oligomers are also referred to in the following as polymers or multimers.

Hence the molecular weight of the intramolecularly, covalently cross-linked proteins is only increased if the chemical linker is covalently bound to the protein, and hence the total mass is slightly increased.

In the case of proteins which are composed of several subunits, the linkage according to the invention only occurs between those subunits which also naturally form an intact protein molecule. This means that the size and the molecular weight of the intramolecularly, covalently cross-linked protein according to the invention is only slightly increased by the cross-linking chemical substance. Linkages within several protein molecules are virtually excluded so that oligomers or even polymers of the proteins form.

According to the invention, the cross-linked proteins can be provided with other modification groups before or after the cross-linking which, for example, are required for their application as labelled antigens or in order to bind the cross-linked proteins to a solid phase. For example, they can be linked with biotin, streptavidin, or with signal-generating labelling groups such as enzymes, fluorescent groups, or chemiluminescent groups. Such modifications are familiar to a person skilled in the art. These modifications should not change the immunological properties of the intramolecularly cross-linked proteins according to the invention, or only to such an extent that a recognition by the specific binding partner in the immunoassay is still ensured.

The almost exclusive intramolecular linkage of the proteins can, for example, be detected by means of SDS polyacrylamide gel electrophoresis (SDS-PAGE) with subsequent Coomassie blue staining, especially in the case of proteins having a quaternary structure.

After the protein cross-linking according to the invention, it should not be possible to detect any molecular weights with the naked eye that are larger than that of the natural molecular weight of the protein in an SDS-PAGE gel. If, for example, a miniaturized commercial SDS-polyacrylamide gradient gel of 8 to 25% polyacrylamide (PHAST system from Pharmacia) is used, the amount of protein applied per lane is about 500 ng. With this amount of protein, molecular weights that are larger than that of the natural molecular weight cannot be detected in this system with the naked eye according to the invention. In the case of proteins which naturally have several subunits, i.e., several polypeptide chains, the molecular weight of a band after cross-linking should not exceed the sum of the molecular weights of the subunits. Protein bands on the gel which have a molecular weight corresponding to the sum of the molecular weights of the subunits may be regarded as a test for a successful intramolecular cross-linking of a protein having a quaternary structure. Hence SDS-PAGE can be used to establish the successful intramolecular cross-linking of a protein consisting of several subunits and the absence of multimers.

Another method for detecting the absence of multimers is by means of gel permeation chromatography, also referred to as gel exclusion chromatography, which can, for example, be carried out using a commercial HPLC apparatus. Protein complexes which have a molecular weight corresponding to a multimer of the individual protein are eluted substantially earlier than proteins that are present singly. According to the invention, only a low percentage of such multimers should be present. If one measures the integral of a HPLC chromatogram, this means that no more than about 5% multimers should be present relative to the eluted peak (integral) of the protein according to the invention which is only cross-linked intramolecularly.

"Immunological binding partners" refers to all molecules which can specifically bind to other molecules under the conditions of an immunoassay. In particular, immunological binding partners should be able to specifically bind the analyte or a substance bound to the analyte. A classical constellation is the specific binding of an antibody to an antigen, for example, the binding of an anti-PSA antibody to PSA. Antibodies and antigens are immunological binding partners. According to the invention, intramolecularly, covalently cross-linked proteins are used as immunological binding partners in immunoassays.

Antigens are preferably used as immunological binding partners when it is intended to detect an antibody directed against these antigens. In this case, the detection of anti-HIV RT antibodies by means of HIV reverse transcriptase that is cross-linked according to the invention is preferred and is described in a later section.

The invention also concerns an immunological test procedure for detecting an analyte in a sample. The method is characterized in that an intramolecularly, covalently cross-linked protein is used as the immunological binding partner. It has turned out that intramolecularly, covalently cross-linked proteins, and in particular, those that are naturally composed of several subunits, are considerably more stable than uncrosslinked proteins under the conditions of an immunoassay.

The various formats and embodiments of immunoassays as well as the various detection methods, such as by means of enzymatic reactions, fluorescent substances, or chemiluminescent substances, are familiar to a person skilled in the art and do not therefore need to be specially elucidated here. A heterogeneous test format is preferred according to the invention in which the solid phase is separated from the liquid phase after completion of the immunological reaction.

The method is preferably an immunoassay for diagnosing HIV infections. If a patient has an HIV infection, this can be detected on the basis of antibodies that have been formed against certain antigens of the virus in a blood, serum or plasma sample. It is often also possible to detect the viral antigens of the HIV itself such as the p24 antigen of HIV-1. This requires the use of specific antibodies directed against the HIV antigen, in this case, against p24.

The detection of an HIV infection in a sample is often carried out as a combined antigen and antibody detection test. Such tests are referred to as COMBI-TESTs. Such a COMBI-TEST is described in WO 98/40744. In this case, HIV antigens, i.e., the p24 antigen of HIV-1 or HIV-1 subtype O and the corresponding p26 antigen of HIV-2, are detected by means of specific antibodies as well as antibodies directed against HIV and specifically against envelope proteins (env) of the pathogen such as gp160, gp120, and gp41 of HIV-1 and gp140, gp110, and gp36 of HIV-2. In addition, antibodies against HIV-RT are also detected in the combitest according to WO 98/40744. For this purpose, HIV-1 reverse transcriptase produced recombinantly is used as an immunological binding partner which, however, is not intramolecularly covalently cross-linked.

According to the invention, intramolecularly, covalently cross-linked RT from HIV, in particular RT from HIV-1, is preferably used in a COMBI-TEST to detect an HIV infection in a sample.

Another subject matter of the invention is intramolecularly, covalently cross-linked reverse transcriptase from HIV, an enzyme which is naturally present in two subunits. The HIV-RT is present as a heterodimer under natural conditions. HIV-1 RT is composed of 1 subunit of 51 kDa and one subunit of 66 kDa. The recombinant form can, for example, be obtained from expression clones (for example, from Müller et al., J. Biol. Chem. 264/24, p. 13975-13978, 1989). Due to a degree of homology of about 60% and even of 100% in some sections at the amino acid level, the HIV-1 RT can in general also be used to detect antibodies directed against HIV-2 RT. The term "HIV" includes HIV-1, HIV-2, and all subtypes and subgroups of the virus such as the HIV-1 subtype O. HIV-1 RT in an intramolecularly, covalently cross-linked form is preferred.

It has surprisingly turned out that the intramolecularly, covalently cross-linked HIV RT is considerably more stable than the uncrosslinked form under the conditions of the immunoassay. The RT according to the invention was considerably better than the uncrosslinked form and withstood temperature stress to which it is, for example, exposed on longer or improper storage or under assay conditions. The intramolecularly, covalently cross-linked RT according to the invention is characterized in that the two subunits are covalently linked together, but there is no intermolecular cross-linking of several molecules. It can, for example, be demonstrated that no oligomers of several RT molecules are present by using gel exclusion chromatography or SDS-PAGE as already elucidated.

Homo- and heterobifunctional linkers are preferably used as cross-linking reagents. In particular, the following are preferably used to intramolecularly cross-link the RT: MHS (3-maleimidobenzoyl-N-hydroxysuccinimide ester), EDC (1-ethyl-3-(3-dimethylaminopropyl)carbodiimide), DSS (disuccinimidylsuberate), HSAB (N-hydroxysuccinimidyl-4-azidobenzoate), and sulfo-SANPAH (sulfosuccinimidyl-6 (4'-amido-2'-nitrophenylamido)hexanoate). As already elucidated, it is important that the chemical reaction of the cross-linking linker only results in an intramolecular cross-linking of the protein or of the two RT subunits but not a cross-linking between several RT molecules. In addition, it is important that no immunologically relevant epitopes are destroyed by the chemical reaction.

Another subject matter of the invention is a method for producing intramolecularly cross-linked HIV reverse transcriptase. The method comprises the steps:

providing RT in a dissolved form, optionally reacting the RT with a blocking reagent for SH groups, dialysing the mixture against aqueous buffer, reacting the activated RT with one of the cross-linking reagents MHS (3-maleimidobenzoyl-N-hydroxysuccinimide ester), EDC (1-ethyl-3-(3-dimethylaminopropyl)carbodiimide), DSS (disuccinimidylsuberate), HSAB (N-hydroxysuccinimidyl-4-azidobenzoate), and sulfo-SANPAH (sulfosuccinimidyl-6(4'-amido-2'-nitrophenylamido)hexanoate), optionally stopping the reaction, separating the excess reactants from the reaction product by dialysis, and optionally exposing the dialysed reaction product to UV light.

The preferred stoichiometry of RT to cross-linking reagent is about 1:1 to 1:20. The ratios of the reactants are selected such that no oligomerization or only a negligible oligomerization occurs between several RT molecules.

The invention is further elucidated by the following examples.

EXAMPLES

Example 1

Intramolecular Cross-linking of HIV-1 Reverse Transcriptase a) Cross-linking with MHS HIV-1 reverse transcriptase (10 mg/ml) was dissolved in 50 mM diethanolamine, pH 8.8, 25 mM NaCl, 1 mM DTT, and 1 mM EDTA. The pH was adjusted to 6.4 by adding a 1 M $KH_2PO_4$ solution.

The mixture was adjusted to 5 mM NMM by adding an appropriate aliquot of a 1 M solution of NMM (N-methylmaleinimide) in DMSO and subsequently incubated for 60 min at 25° C. while stirring. It was subsequently dialysed against 50 mM diethanolamine, pH 8.8, 25 mMNaCl.

The pH was then adjusted to pH 7.0 by adding a 1 M $KH_2PO_4$ solution. A stock solution of MHS (3-maleimidobenzoyl-N-hydroxysuccinimide ester) was prepared in DMSO (5 mg/ml). A quantity of this solution corresponding to an initial stoichiometry of 1:8 (mol reverse transcriptase/mol MHS) was added to the mixture which was then incubated for a further 60 min at 25° C. while stirring. The reaction was terminated by adding lysine to the reaction mixture at a final concentration of 10 mM and incubating for a further 30 min. Excess reactants were separated by dialysis against 10 mm potassium phosphate buffer, pH 6.0, 50 mM NaCl, 1 mM EDTA.

After dialysis the pH was adjusted to 7.4 by adding an aliquot of a 1 M $K_2HPO_4$ solution. The mixture was incubated for a further 4 h at 25° C. while stirring, before adding cysteine to a final concentration of 2 mM. After a further 30 min incubation, the reaction was terminated by adding NMM (final concentration 5 mM). The mixture was dialysed against 50 mM diethanolamine, pH 8.8, 25 mM NaCl.

b) Cross-linking with EDC

HIV-1 reverse transcriptase (10 mg/ml) was dissolved in 50 mM diethanolamine, pH 8.8, 25 mM NaCl, 1 mM DTT, and 1 mM EDTA. The pH was adjusted to 6.4 by adding a 1 M $KH_2PO_4$ solution.

The mixture was made up to 5 mM NMM by adding an appropriate aliquot of a 1 M solution of NMM (N-methylmaleinimide) in DMSO and subsequently incubated for 60 min at 25° C. while stirring. It was subsequently dialysed against 10 mM potassium phosphate buffer, pH 7.0, 50 mM NaCl.

A stock solution of EDC (1-ethyl-3-(3-dimethylaminopropyl)carbodiimide) was prepared in DMSO (2 mg/ml). A quantity of this solution corresponding to an initial stoichiometry of 1:10 (mol reverse transcriptase/mol EDC) was added to the mixture, which was then incubated for a further 60 min at 25° C. while stirring. Excess reactants were separated by dialysis against 25 mM potassium phosphate buffer, pH 7.0, 50 mM NaCl.

c) Cross-linking with DSS

HIV-1 reverse transcriptase (10 mg/ml) was dissolved in 50 mM diethanolamine, pH 8.8, 25 mM NaCl, 1 mM DTT, and 1 mM EDTA. The pH was adjusted to 6.4 by adding a 1 M $KH_2PO_4$ solution.

The mixture was made up to 5 mM NMM by adding an appropriate aliquot of a 1 M solution of NMM (N-methylmaleinimide) in DMSO and subsequently incubated for 60 min at 25° C. while stirring. It was subsequently dialysed against 10 mM potassium phosphate buffer, pH 8.0, 25 mM NaCl.

A stock solution of DSS (disuccinimidyl suberate) was prepared in DMSO (2 mg/ml). A quantity of this solution corresponding to an initial stoichiometry of 1:10 (mol reverse transcriptase/mol DSS) was added to the mixture, which was then incubated for a further 60 min at 25° C. while stirring. Excess reactants were separated by dialysis against 25 mM potassium phosphate buffer, pH 7.0, 50 mM NaCl.

d) Cross-linking with HSAB

HIV-1 reverse transcriptase (10 mg/ml) was dissolved in 50 mM diethanolamine, pH 8.8, 25 mM NaCl, 1 mM DTT, and 1 mM EDTA. The pH was adjusted to 6.4 by adding a 1 M $KH_2PO_4$ solution.

The mixture was made up to 5 mM NMM by adding an appropriate aliquot of a 1 M solution of NMM (N-methylmaleinimide) in DMSO and subsequently incubated for 60 min at 25° C. while stirring. It was subsequently dialysed against 10 mM potassium phosphate buffer, pH 8.0, 25 mM NaCl.

A stock solution of HSAB (N-hydroxysuccinimidyl-4-azidobenzoate) was prepared in DMSO (2 mg/ml). A quantity of this solution corresponding to an initial stoichiometry of 1:5 (mol reverse transcriptase/mol HSAB) was added to the mixture, which was then incubated for a further 60 min at 25° C. while stirring. Excess reactants were separated by dialysis against 25 mM potassium phosphate buffer, pH 7.0, 50 mM NaCl.

The mixture was subsequently irradiated for 7 min with a UV lamp.

e) Cross-linking with Sulfo-SANPAH

HIV-1 reverse transcriptase (10 mg/ml) was dissolved in 50 mM diethanolamine, pH 8.8, 25 mM NaCl, 1 mM DTT, and 1 mM EDTA. The pH was adjusted to 6.4 by adding a 1 M $KH_2PO_4$ solution.

The mixture was made up to 5 mM NMM by adding an appropriate aliquot of a 1 M solution of NMM (N-methyl-maleinimide) in DMSO and subsequently incubated for 60 min at 25° C. while stirring. It was subsequently dialysed against 10 mM potassium phosphate buffer, pH 8.0, 25 mM NaCl.

A stock solution of sulfo-SANPAH (sulfosuccinimidyl-6 (4'-amido-2'-nitrophenyl-amido)hexanoate) was prepared in DMSO (4 mg/ml). A quantity of this solution corresponding to an initial stoichiometry of 1:5 (mol reverse transcriptase/mol sulfo-SANPAH) was added to the mixture, which was then incubated for a further 60 min at 25° C. while stirring. Excess reactants were separated by dialysis against 25 mM potassium phosphate buffer, pH 7.0, 50 mM NaCl.

The mixture was subsequently irradiated for 7 min with a UV lamp.

Example 2

Detection of the Exclusive Intramolecular Cross-linking of HIV-1 Reverse Transcriptase a) SDS Gel Electrophoresis Aliquots of the intramolecularly cross-linked HIV-1 reverse transcriptase were analysed by polyacrylamide gel electrophoresis in the presence of SDS on a PHAST gel apparatus (Pharmacia) according to a standard protocol of the manufacturer.

The non-cross-linked control only has bands with molecular weights of 66 kD and 51 kD which correspond to the subunits of the reverse transcriptase. Intramolecularly cross-linked reverse transcriptase exhibits bands with molecular weights of 110-120 kD, which demonstrates a successful cross-linking between subunits. Larger protein complexes are not detectable, i.e., an intramolecular linkage of several molecules of reverse transcriptase does not occur with the cross-linking method according to the invention.

b) Analytical Gel Permeation Chromatography

An aliquot of the intramolecularly cross-linked HIV-1 reverse transcriptase was analysed by gel permeation chromatography on a TSK 3000 column (Toso Haas) using a commercial HPLC apparatus according to a standard protocol of the manufacturer.

The intramolecularly cross-linked reverse transcriptase elutes from the column with a retention time that corresponds to globular proteins having molecular weights of 100-130 kD (in this case 7.5 min). Larger protein complexes which would have a shorter retention time in the chromatogram are not detectable, i.e., the cross-linking method according to the invention does not result in an intermolecular cross-linking of several molecules of reverse transcriptase to form oligomeric or polymeric structures. The chromatogram is shown in FIG. 1.

Example 3

Derivatization of Intramolecularly Cross-linked HIV-1 Reverse Transcriptase with a Biotin Label Intramolecularly cross-linked HIV-1 reverse transcriptase (see example 1) was present in diethanolamine or potassium phosphate buffer. The uncrosslinked RT was treated as a comparison with N-methylmaleimide and dialysed against diethanolamine. If necessary, the pH was adjusted to 8.6-8.8 in all RT mixtures by adding NaOH. A stock of biotin-DDS (biotinyl-diaminodioxaoctane-disuccinimidyl suberate) was prepared in DMSO (6 mg/ml). A quantity of this solution corresponding to an initial stoichiometry of 1:4 (mol reverse transcriptase/mol biotin-DDS) was added to the mixture, which was then incubated for a further 60 min at 25° C. while stirring. The reaction was terminated by adding lysine to the reaction mixture to a final concentration of 10 mM and incubating for a further 30 min. Excess reactants were separated by dialysis against 50 mM diethanolamine, pH 8.8, 25 mM NaCl.

Example 4

Stability Check in a Function Test

An immunoassay was carried out on an ELECSYS® analyzer from Roche Diagnostics GmbH, Mannheim, to examine the stability of the HIV-1 reverse transcriptase. In addition to a negative control (NC) which contained no anti-RT antibodies and a positive control (PC) which contained anti-RT antibodies, two HIV-positive human sera with anti-RT reactivity were measured. 45 µl sample was incubated together with 55 µl Reagent 1 (biotinylated RT) and 55 µl Reagent 2 (ruthenium-labelled RT) for 9 min at 37° C. Subsequently streptavidin-coated magnetic beads were added, and the mixture was incubated for a further 9 min. Afterwards the beads were captured by a magnet, and the electrochemilumine-scence signal was quantified.

In order to compare the stability of biotinylated reverse transcriptase in the cross-linked form according to the invention and in an uncrosslinked form, Reagent 1 (biotinylated RT) was incubated for 18 hours at 42° C. as described below before carrying out the test.

Reagent 1, which was prepared at the same time and stored at 4° C., served as a reference. All other reagents were freshly prepared for the experiments.

The evaluation was based on the dynamic range of the signal which means that one determines the quotients of the signal and the respective negative control. The larger the value for signal dynamics the greater is the differentiation between HIV antibody-positive and negative samples. Hence a large dynamic range of the signal is desirable. The relation between the respective values was used to compare stressed RT and unstressed RT. The results are shown in Table 1.

TABLE 1

| Samples | Unstressed | | Stress 18 h 42° C. | | Comparison stressed/unstressed | |
|---|---|---|---|---|---|---|
| | Counts | Signal dynamic range | Counts | Signal dynamic range | Counts | Signal dynamic range |
| Recombinant HIV-1-RT-Bi(DDS), non-cross-linked | | | | | | |
| Negative control | 1763 | 1.0 | 1049 | 1.0 | 60% | 100% |
| Positive control | 16848 | 9.6 | 1480 | 1.4 | 9% | 15% |
| HIV serum 1 | 6209 | 3.5 | 1054 | 1.0 | 17% | 29% |
| HIV serum 2 | 5162 | 2.9 | 917 | 0.9 | 18% | 30% |
| HIV serum 3 | 5832 | 3.3 | 1150 | 1.1 | 20% | 33% |
| HIV serum 4 | 111444 | 63.2 | 6267 | 6.0 | 6% | 9% |
| Recombinant HIV-1-RT (MHS)-Bi(DDS), cross-linked according to the invention | | | | | | |
| Negative control | 1304 | 1.0 | 1206 | 1.0 | 92% | 100% |
| Positive control | 73335 | 56.2 | 77611 | 64.4 | 106% | 114% |
| HIV serum 5 | 8476 | 6.5 | 7092 | 5.9 | 84% | 90% |
| HIV serum 6 | 14504 | 11.1 | 10615 | 8.8 | 73% | 79% |
| HIV serum 7 | 69459 | 53.3 | 59347 | 49.2 | 85% | 92% |
| HIV serum 8 | 168674 | 129.4 | 168304 | 139.6 | 100% | 108% |

Even after stress for several hours at an elevated temperature, the dynamic range of the signal in the immunoassay using RT cross-linked according to the invention was still at least 79% and preferably at least 90% compared to unstressed RT, whereas the dynamic range based on the negative control was at most about 30% and sometimes considerably less than 30% or even below 20% in the case of uncrosslinked RT. When using uncrosslinked RT, the signal dropped to the level of negative sera, whereas the cross-linked RT according to the invention retains its immunological function. Hence the RT epitopes recognized by the sample antibody are substantially preserved despite the thermal stress. This means that the cross-linked RT according to the invention is considerably more stable than uncrosslinked RT.

What is claimed is:

1. A method for detecting an analyte in a sample comprising the steps of:
    a. combining the sample with an intramolecularly, covalently cross-linked HIV reverse transcriptase in the absence of detectable intermolecular multimers of the HIV reverse transcriptase, wherein the HIV reverse transcriptase specifically binds with the analyte or with a substance bound to the analyte to form a complex,
    b. adding to the combination formed in step (a) a binding partner provided with a label that combines with the complex formed in step (a) to produce a detectable signal, and
    c. determining the signal produced in step (b) as a measure of the analyte in the sample.

2. The method of claim 1 wherein the analyte is an anti-HIV reverse transcriptase antibody.

3. A method for detecting an analyte in a sample comprising the steps of:
    a. contacting the sample with a composition comprising an intramolecularly, covalently cross-linked HIV reverse transcriptase, wherein said composition comprises less than about 5% of total intermolecular multimers of HIV reverse transcriptase relative to the eluted peak intramolecularly, covalently cross-linked HIV reverse transcriptase as determined in a gel permeation chromatograph, wherein the intramolecularly, covalently cross-linked HIV reverse transcriptase specifically binds with the analyte or with a substance bound to the analyte to form a complex,
    b. adding to the combination formed in step (a) a binding partner provided with a label that combines with the complex formed in step (a) to produce a detectable signal, and
    c. determining the signal produced in step (b) as a measure of the analyte in the sample.

4. The method of claim 3 wherein the intermolecular multimers of HIV reverse transcriptase are undetectable using SDS-PAGE analysis when 500 ng of said composition is loaded per lane.

5. The method of claim 3 wherein the intermolecular multimers of HIV reverse transcriptase are undetectable in said composition as determined by gel permeation chromatography analysis.

6. The method of claim 4 wherein the analyte is an anti-HIV reverse transcriptase antibody.

7. The method of claim 6 wherein HIV reverse transcriptase is cross-linked, to form said intramolecularly, covalently cross-linked HIV reverse transcriptase, using a cross-linking agent selected from the group consisting of MHS (3-maleimidobenzoyl-N-hydroxysuccinimide ester), EDC (1-ethyl-3-(3-dimethylaminopropyl)carbodiimide), DSS (disuccinimidylsuberate), HSAB (N-hydroxysuccinimidyl-4-azidobenzoate), and sulfo-SANPAH (sulfosuccinimidyl-6(4'-amido-2'-nitrophenylamido)hexanoate).

8. The method of claim 6 wherein the intramolecularly, covalently cross-linked HIV reverse transcriptase is further modified to comprise a signal generating group or a ligand for binding to a solid support.

9. The method of claim 8 wherein the signal generating group is selected from the group consisting of enzymes, fluorescent groups and chemiluminescent groups.

10. The method of claim 8 wherein the ligand is biotin or streptavidin.

11. The method of claim 1 wherein the intramolecularly, covalently cross-linked HIV reverse transcriptase is further modified to comprise a signal generating group or a ligand for binding to a solid support.

12. The method of claim 1 wherein the intramolecularly, covalently cross-linked HIV reverse transcriptase is covalently linked to biotin or streptavidin.

* * * * *